United States Patent [19]

Yamauchi et al.

[11] Patent Number: 4,721,788
[45] Date of Patent: Jan. 26, 1988

[54] 4-CYANOPIPERIDINE DERIVATIVES

[75] Inventors: Hiroshi Yamauchi; Seiichiro Nomoto, both of Ibaraki; Isao Sugiyama; Yuuki Komatu, both of Ibaraki; Takeo Kanai, Chiba; Keizo Takayanagi, Gumma; Yasuhide Tanaka, Saitama; Atsushi Koiwa, Chiba; Shinichi Endoh, Ibaraki, all of Japan

[73] Assignee: Eisai Co., Ltd., Tokyo, Japan

[21] Appl. No.: 883,697

[22] Filed: Jul. 8, 1986

[30] Foreign Application Priority Data

Jul. 12, 1985 [JP] Japan .................................. 60-152439

[51] Int. Cl.$^4$ ........................................... C07D 211/26
[52] U.S. Cl. .................................................... 546/246
[58] Field of Search ......................................... 546/246

[56] References Cited

U.S. PATENT DOCUMENTS 3,118,926 1/1964 Horrom .......................... 558/460 X
4,426,386 1/1984 Arvidsson et al. ............. 546/246 X

FOREIGN PATENT DOCUMENTS 1415682 11/1975 United Kingdom ................ 546/246
1420759 1/1976 United Kingdom ................ 546/246

OTHER PUBLICATIONS

Noller, "The Chemistry of Organic Compounds", 3rd Ed., (1965), p. 253; [W. B. Saunders Co., Philadelphia & London].

Primary Examiner—Joseph Paul Brust
Attorney, Agent, or Firm—Wenderoth, Lind & Ponack

[57] ABSTRACT

A novel 4-cyanopiperidine derivative, which is represented by the following general formula (I):

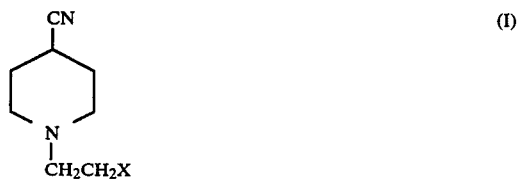

wherein X means a halogen atom, or an acid addition salt thereof, is prepared by reacting N-(2-hydroxyethyl)-4-carbamoylpiperidine or an acid addition salt thereof with a dehydrating and halogenating agent; or by reacting 4-cyanopiperidine or a salt thereof with a compound represented by the following general formula (IV):

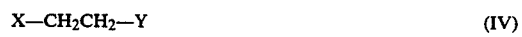

X—CH$_2$CH$_2$—Y (IV)

wherein X has the same meaning as defined above and Y denotes the same halogen atom as X or another halogen atom. The derivative is useful as intermediate for synthesis of quinuclidine derivative which is in turn useful as intermediate for the production of medicines, chemicals, etc.

5 Claims, No Drawings

4-CYANOPIPERIDINE DERIVATIVES

BACKGROUND OF THE INVENTION (1) Field of the Invention

This invention relates to novel 4-cyanopiperidine derivatives and a process for the preparation of same.

(2) Description of the Prior Art

The compounds of this invention are useful as intermediates for the syntheses of quinuclidine derivatives. Quinuclidine derivatives are in turn useful as synthesis intermediates for medicines, chemical reagents, etc. Their syntheses are however not easy due to their unique structures. Synthetic processes for quinuclidine derivatives have been reported, for example, in Helvetica Chimica Acta, 194, 1672–1679 (1954) and ibid, 195, 1680–1688 (1954). In this literature, 4-cyanoquinuclidine was synthesized by way of N-methyl-4-carbamoylpiperidine, N-methyl-4-cyanopiperidine and N-methyl-4-cyanoquinuclidine when 4-carbamoylpiperidine was employed as a starting material. This synthetic route however involved problems such that many process steps were required because N-methylation was effected at the beginning and demethylation was conducted at the end and the yield of the conversion step of from piperidine to quinuclidine was as low as 17%.

SUMMARY OF THE INVENTION

The present inventors have found that the use of compounds of this invention allows one to obtain quinuclidine derivatives with ease, resulting in completion of the present invention.

An object of this invention is therefore to provide novel 4-cyanopiperidine derivatives useful as synthesis intermediates for quinuclidine derivatives and a process for their preparation.

In one aspect of this invention, there is thus provided a 4-cyanopiperidine derivative represented by the following general formula (I):

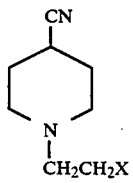

(I)

wherein X means a halogen atom, or an acid addition salt thereof.

In another aspect of this invention, there is also provided a process for the preparation of a 4-cyanopiperidine derivative represented by the following general formula (I):

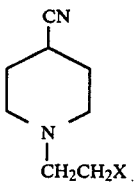

(I)

wherein X means a halogen atom, or an acid addition salt thereof, which comprises reacting a compound represented by the following formula (II):

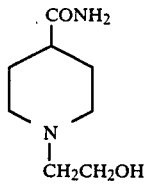

(II)

or an acid addition salt thereof with a dehydrating and halogenating agent.

In a further aspect of this invention, there is also provided a process for the preparation of a 4-cyanopiperidine derivative represented by the following general formula (I):

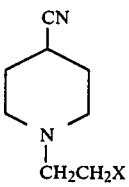

(I)

wherein X means a halogen atom, or an acid addition salt thereof, which comprises reacting a compound represented by the following formula (III):

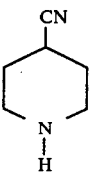

(III)

or an acid addition salt thereof with a compound represented by the following general formula (IV):

X—CH$_2$CH$_2$—Y     (IV)

wherein X has the same meaning as defined above and Y denotes the same halogen atom as X or another halogen atom.

The novel 4-cyanopiperidine derivatives of this invention are useful for the easy syntheses of quinuclidine derivatives.

The above and other objects, features and advantages of the present invention will become apparent from the following description and the appended claims.

DETAILED DESCRIPTION OF THE INVENTION AND PREFERRED EMBODIMENTS

As the halogen atom represented by X in the general formula (I), a chlorine atom, bromine atom, iodine atom or the like may be mentioned. Illustrative of the acid addition salt of the compound represented by the general formula (I) may include inorganic acid addition salts such as hydrochloride, hydrobromide, hydroiodide, sulfate, carbonate and bicarbonate; organic carboxylates such as acetate, maleate, lactate, tartrate and trifluoroacetate; organic sulfonates such as methanesulfonate, benzenesulfonate and toluenesulfonate; amino acid salts such as aspartate and glutamate; etc.

The compound (I) of this invention can be prepared by the following processes:

Preparation Process A

The compound represented by the formula (II) or its acid addition salt is reacted with a dehydrating and halogenating agent to obtain the compound of the general formula (I) or its acid addition salt.

The term "dehydrating and halogenating agent" as used herein means a reagent which has both dehydrating function and halogenating function. As exemplary dehydrating and halogenating agents, may be mentioned thionyl chloride, thionyl bromide, thionyl iodide, phosphorus oxychloride, phosphorus oxybromide and the like.

The above reaction can be carried out in a solvent such as benzene, toluene, xylene, acetonitrile, dioxane or tetrahydrofuran or a mixed solvent of two or more of such solvents at a temperature ranging from 10° C. to the refluxing temperature of the solvent.

Examples of the acid addition salt of the compound of the formula (II), which acid addition salt salt is also useful in the above reaction, may include those similar to the above-described acid addition salts of the compound of the general formula (I).

Preparation Process B

The compound represented by the formula (III) or its acid addition salt is reacted with the compound represented by the general formula (IV) to obtain the compound of the general formula (I) or its acid addition salt.

As exemplary halogen atoms represented by X and Y in the general formula (IV), may be mentioned chlorine atom, bromine atom and iodine atom. As specific compounds of the general formula (IV), there are 1-bromo-2-chloroethane, 1,2-dichloroethane, 1,2-dibromoethane, 1-iodo-2-chloroethane, 1-iodo-2-bromoethane, 1,2-diiodoethane and so on.

The above reaction can be conducted in a solvent such as methanol, ethanol, isopropanol, n-propanol, n-butanol or dimethylformamide or a mixed solvent of two or more of such solvents at a temperature ranging from room temperature to the refluxing temperature of the solvent.

Examples of the acid addition salt of the compound of the formula (III), which acid addition salt is also useful in the above reaction, may include those similar to the above-described acid addition salts of the compound of the general formula (I).

The present invention will hereinafter be described in further detail by the following Experiments and Examples. It should however be borne in mind that the present invention is not necessarily limited to or by the following Experiments and Examples.

Experiment 1

N-(2Hydroxyethyl)-4-carbamoylpiperidine

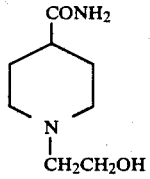

2-Chloroethanol (23.9 ml), potassium carbonate (82.0 g) and sodium iodide (4.5 g) were added to an ethanol solution (500 ml) of 4-carbamoylpiperidine (35 g), followed by refluxing for 20 hours. After allowing the reaction mixture to cool down to room temperature, it was filtered through Celite (trade mark). The filtrate was concentrated under reduced pressure. After washing the residue, it was dried to obtain 46.6 g of the desired product.

Melting point: 141°–142° C.

IR absorption spectrum (cm$^{-1}$, Nujol ®): 3360, 3160, 1650, 1610.

NMR spectrum (δ, DMSO-d$_6$): 1.2–2.1 (7H, m), 2.26 (2H, t, J=8 Hz) 2.6–2.9 (2H, m), 4.39 (2H, t, J=8 Hz), 4.32 (1H, br.s), 6.59 (1H, br.s), 7.11 (1H, br.s),

EXAMPLE 1

N-(2-Chloroethyl)-4-cyanopiperidine.HCl

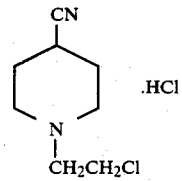

To a suspension of the compound (38.7 g) of Experiment 1 in acetonitrile (390 ml), thionyl chloride (82 ml) was added dropwise over 1 hour with ice-cooling and stirring. After refluxing the resulting solution for 4 hours, it was concentrated. Isopropanol (100 ml) was added to the residue, followed by refluxing for 10 minutes. The solution was allowed to cool down to room temperature and the resulting crystals were collected by filtration. Besides, isopropyl ether was added to the filtrate and the resulting crystals were also collected by filtration. As colorless crystals, the desired product was obtained in a total amount of 43.1 g.

Melting point: 176°–178° C.

IR absorption spectrum (cm$^{-1}$, Nujol ®): 2220.

NMR spectrum (δ, DMSO-d$_6$): 1.7–2.3 (4H, m), 2.6–3.8 (7H, m), 3.98 (2H, t, J=8 Hz).

EXAMPLE 2

N-(2-Chloroethyl)-4-cyanopiperidine

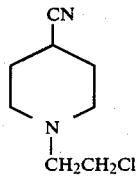

1-Bromo-2-chloroethane (2.6 ml) and potassium carbonate (6.6 g) were added to a solution of 4-cyanopiperidine (2.63 g) in isopropanol (50 ml), followed by refluxing for 10 hours. The reaction mixture was concentrated under reduced pressure. After adding a 50% aqueous solution of potassium carbonate to the residue, the resulting mixture was extracted with diethyl ether. The extract was washed with saturated saline, followed by an addition of anhydrous potassium carbonate to dry the diethyl ether solution. The thus-dried diethyl ether solution was concentrated under reduced pressure. The residue was purified by silica gel chromatography (developer: methanol-chloroform) to obtain 0.31 g of the desired product in an oily form.

IR absorption spectrum (cm$^{-1}$ neat): 2220.

NMR spectrum (δ, CDCl$_3$): 1.7–2.1 (4H, m), 2.3–2.9 (7H, m), 3.56 (2H, t, J=8 Hz).

Illustrative syntheses of 4-cyanoquinuclidine from the above-obtained compounds of this invention will next be described.

Experiment 2

4-Cyanoquinuclidine and its p-toluene sulfonate

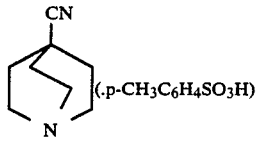

Sodium amide (150 g) and sodium iodide (7.2 g) were suspended in 1,2-dimethoxyethane (1.5 l), and the resulting suspension was stirred at room temperature for 1 hour. The compound (100 g) of Example 1 was then added to the suspension and the resulting mixture was stirred for 24 hours. The reaction mixture was poured in ice water (2 l), followed by filtration through Celite (trade mark). The residue was washed with diethyl ether (300 ml). The organic layer of the filtrate was combined with the washing, followed by an addition of anhydrous potassium carbonate to dry same. The thus-dried solution was then concentrated to obtain 4-cyanoquinuclidine (78.7 g). In addition, after adding anhydrous potassium carbonate (1 kg) to the water layer of the filtrate, the resulting mixture was extracted with chloroform. After adding anhydrous potassium carbonate to the extract to dry same, the thus-dried chloroform solution was concentrated to obtain 4-cyanoquinuclidine (18.9 g). In total, 97.6 g of 4-cyanoquinuclidine was obtained (yield: 66.3%).

4-Cyanoquinuclidine (85.0 g) was suspended in ethanol (200 ml), followed by an addition of a solution of p-toluenesulfonic acid monohydrate (119 g) in ethanol (350 ml). The resulting mixture was then stirred at 40° C. for 1 hour. The reaction mixture was cooled with ice and the precipitated crystals were collected by filtration. They were then washed with ethanol and diethylether to obtain 182.9 g of 4-cyanoquinuclidine p-toluenesulfonate as colorless crystals (yield: 95%).

4-Cyanoquinuclidine:
Melting point: 133° C.
IR absorption spectrum (cm$^{-1}$, Nujol ®): 2225.
NMR spectrum (δ, CDCl$_3$): 1.6–2.0 (6H, m), 2.7–3.0 (6H, m).

4-Cyanoquinuclidine p-toluenesulfonate:
Melting point: 220° C.
IR absorption spectrum (cm$^{-1}$, Nujol ®): 2220.
NMR spectrum (δ, DMSO-d$_6$): 2.0–2.3 (6H, m), 2.27 (3H, s), 3.1–3.5 (6H, m), 7.08. (2H, d, J=10 Hz), 7.45 (2H, d, J=10 Hz).

Experiment 3

4-Cyanoquinuclidine

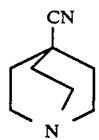

n-Butyl lithium (19.9 ml) was added at −78° C. to a solution of diisopropylamine (4.7 ml) in tetrahydrofuran (70 ml), followed by stirring for 10 minutes. To the resulting lithium diisopropylamide solution, a solution of the compound (5.0 g) of Example 2 in tetrahydrofuran (30 ml) was added dropwise at the same temperature over 10 minutes. After stirring the resulting mixture at the same temperature for 20 minutes, it was stirred at 0° C. for further 30 minutes. The reaction solution was washed with saturated saline, followed by extraction with chloroform. The extract was concentrated and the residue was then sublimated to obtain 2.6 g of the desired product (yield: 65.3%).

Melting point: 133° C.
IR absorption spectrum (cm$^{-1}$, Nujol ®): 2225.
NMR spectrum (δ, CDCl$_3$): 1.6–2.0 (6H, m), 2.7–3.0 (6H, m).

Having now fully described the invention, it will be apparent to one of ordinary skill in the art that many changes and modifications can be made thereto without departing from the spirit or scope of the invention as set forth herein.

We claim:

1. A 4-cyanopiperidine derivative represented by the following general formula (I):

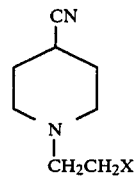

wherein X represents a halogen atom, or a medicinally acceptable acid addition salt thereof.

2. The compound as claimed in claim 1, wherein X means a chlorine, bromine or iodine atom.

3. The compound as claimed in claim 1, wherein the acid addition salt is selected from the group consisting of inorganic acid addition salts, organic carboxylates, organic sulfonates, and amino acid salts.

4. The compound as claimed in claim 3, wherein the inorganic acid addition salts are hydrochloride, hydrobromide, hydroiodide, sulfate, carbonate and bicarbonate; the organic carboxylates are acetate, maleate, lactate, tartrate and trifluoroacetate; the organic sulfonates are methanesulfonate, benzenesulfonate and toluenesulfonate; and the amino acid salts are aspartate and glutamate.

5. The compound as claimed in claim 1, which is N-(2-chloroethyl)-4-cyanopiperidine or an acid addition salt thereof.

* * * * *